US00PP14596P29

(12) United States Plant Patent
Dickson

(10) Patent No.: US PP14,596 P2
(45) Date of Patent: Mar. 9, 2004

(54) HYBRID TEA ROSE PLANT NAMED 'DICWISP'

(50) Latin Name: *Rosa hybrida*
Varietal Denomination: DICwisp

(75) Inventor: Colin Dickson, Newtownards (GB)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/241,662

(22) Filed: Sep. 10, 2002

(51) Int. Cl.[7] ..... A01H 5/00
(52) U.S. Cl. ..... Plt./133
(58) Field of Search ..... Plt./133, 130, 134

*Primary Examiner*—Howard J. Locker
(74) *Attorney, Agent, or Firm*—Klarquist Sparkman, LLP

(57) ABSTRACT

Hybrid tea rose plant having vigorous, upright growth; long cutting stems; large, high-centered blooms; attractive, near white flower color; and excellent disease resistance.

1 Drawing Sheet

Genus and species: *Rosa hybrida.*
Variety denomination: DICwisp.

SUMMARY OF THE INVENTION

The present invention relates to a new and distinct variety of rose plant named DICwisp of the hybrid tea class which was originated by me by crossing the variety MACyefre, (unpatented), with the variety DICjana, (unpatented).

BACKGROUND OF THE INVENTION

The primary objective of this breeding was to produce a new rose variety having the vigorous, upright growth and disease resistance of the female parent combined with the large, high-centered blooms, disease resistant foliage and profuse blooming of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous, upright growth;
2. Long cutting stems;
3. Large, high-centered blooms;
4. Attractive, near white flower color; and
5. Excellent disease resistance.

Asexual reproduction of this new variety by budding, as performed at Somis, Calif. and Wasco, Calif., shows that the foregoing and all other characteristics and distinctions come true to form and are established and transmitted through succeeding propagations.

COMPARISON WITH PARENTS

MACyefre has yellow flowers; DICjana has pale yellow flowers; and DICwisp has near white flowers.

COMPARISON WITH SIMILAR VARIETY

The closest variety is JAColite, whose flowers have 25 petals (10 less than DICwisp), has larger foliage and fewer blooms.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—MACyefre.
*Pollen parent.*—DICjana.

FLOWER

Observations made January—December 2001 from plants beginning at two years of age grown in a garden environment at Somis, Calif.

Blooming habit: Continuous.
Bud:
*Size.*—4–6 cm. long when the petals start to unfurl.
*Form.*—The bud form is long, pointed ovoid.
*Color.*—When sepals first divide, bud color is White Group 155A. When half blown, the upper sides of the petals are Yellow-White Group 158D; and the lower sides of the petals are White Group 155D.
*Sepals.*—Color: Upper Surface: Green Group 142C. Lower Surface: Green Group 137C, often with Greyed-Purple Group 184B in center. Length: 40–50 mm. Width: 11–13 mm. Shape: Obovate. Surface texture: Upper: Hoary, Lower: Smooth. There are three lightly appendaged sepals. There are two unappendaged sepals with hairy edges.

*Receptacle.*—Color: Green Group 137C. Shape: Funnel. Size: Small, about 5–7 mm long×6–8 mm wide. Surface: Smooth.

*Peduncle.*—Length: Long, averaging about 15–20 cm. Surface: Smooth. Color: Green Group 137C. Strength: Stiff, erect.

Bloom:

*Size.*—Large. Average open size is 12–14 cm.

*Borne.*—Singly.

*Stems.*—Strength Strong. Average length is about 40–45 cm.

*Form.*—When first open: High centered. Permanence: All petals curl back quill fashion.

*Petalage.*—Number of petals under normal conditions: 30–35.

*Color.*—The upper sides of the petals are Yellow-White Group 158D. The reverse sides of the petals are White Group 155D. The base of each petal is Yellow Group 6D. The major color on the upper side is Yellow-White Group 158D.

*Variegations.*—None.

*Discoloration.*—The general tonality at the end of the first day: Yellow-White Group 158D. At the end of the third day: Yellow-White Group 158D.

*Fragrance.*—Slight. Character of fragrance: Musk.

Petals:

*Texture.*—Thick.

*Shape.*—Round.

*Margin.*—Slightly sinuate.

*Apex shape.*—Obtuse.

*Base shape.*—Widely cuneate.

*Form.*—Moderately quilled.

*Arrangement.*—Imbricated.

*Petaloids.*—Number: 1–3. Color: Yellow-White Group 158D.

*Persistence.*—Petals drop off cleanly before drying.

*Lastingness.*—On the plant: Long (about 5–7 days). As a cut flower: Long (about 7–9 days).

Reproductive parts:

*Stamens.*—Number: 140–160. Length: 12–15 mm. Anthers: Length: 2–3 mm. Color: Yellow-Orange Group 14C. Arrangement: Regular around styles. Filaments: Color: Yellow Group 8C. Length: 10–12 mm. Pollen: Color: None observed.

*Pistils.*—Number: 80–100. Styles: Color: Red Group 43C. Length: 2–8 mm. Stigmas: Color: Yellow-Orange Group 16C. Length: 1 mm.

*Hips.*—None observed.

Plant:

*Form.*—Bush.

*Growth.*—Vigorous.

*Mature plant.*—Age: Two years. Height: 160–180 cm; Width: 100–120 cm.

*Rootstock.*—Dr. Huey.

Foliage: Number of leaflets on normal mid-stem leaves.

*Size.*—Medium (12–15 cm long×10–12 cm wide).

*Quantity.*—Normal.

*Color.*—New foliage: Upper side: Greyed-Purple Group 187A. Lower side: Greyed-Purple Group 183B. Old foliage: Upper side: Green Group 139A. Lower side: Green Group 137C.

Leaflets:

*Size.*—Width: 3–4 cm. Length: 4–6 cm.

*Shape.*—Broadly oval. Base Shape: Cuneate. Apex Shape: Cuspidate.

*Texture.*—Glossy.

*Edge.*—Serrated.

*Serrations.*—Single.

*Petiole color.*—Yellow-Green Group 145A.

*Petiole rachis.*—Color: Upper: Yellow-Green Group 146B; Lower: Yellow-Green Group 146C. Underside: Smooth with occasional prickles.

*Stipules.*—Length: 25–30 mm, serrated. Color: Yellow-Green Group 145A.

*Disease resistance.*—Resistant to mildew, blackspot and rust under normal growing conditions.

*Pest persistence.*—Not tested.

*Vein color.*—Yellow-Green Group 145A.

*Venation pattern.*—Costate.

Wood:

*New wood.*—Color: Yellow-Green Group 147B. Bark: Smooth.

*Old wood.*—Color: Green Group 137C. Bark: Smooth.

Prickles:

*Quantity.*—On main canes from base: None. On laterals from main canes: Ordinary.

*Form.*—Straight. Length: 5–8 mm.

*Color when young.*—Red Group 53A.

*Color when mature.*—Greyed-Orange Group 165B.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by its vigorous, upright growth; long cutting stems; large, high-centered blooms; attractive near white flower color; and excellent disease resistance.

* * * * *

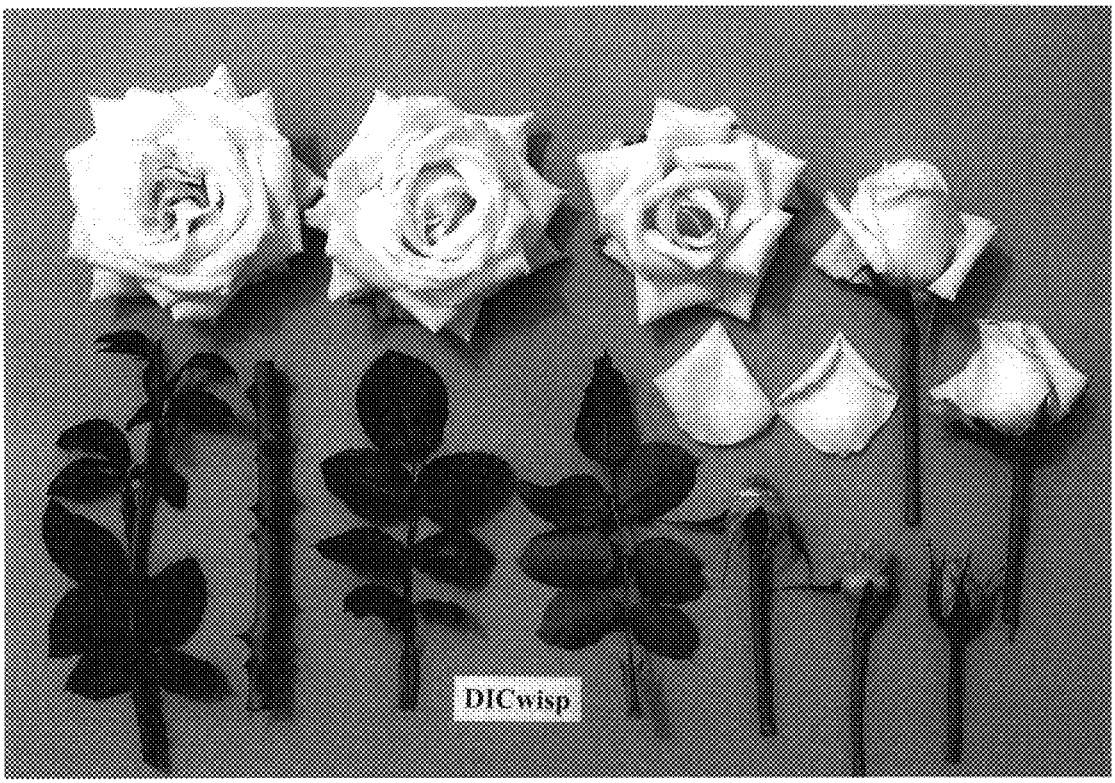
DICwisp

UNITED STATES PATENT AND TRADEMARK OFFICE

CERTIFICATE OF CORRECTION

PATENT NO. : PP 14,596 P2
DATED : March 9, 2004
INVENTOR(S) : Colin Dickson

It is certified that error appears in the above-identified patent and that said Letters Patent is hereby corrected as shown below:

Column 4,
Line 7, “leaves.” should read -- leaves: 5-7. --

Signed and Sealed this

Twenty-second Day of June, 2004

JON W. DUDAS
*Acting Director of the United States Patent and Trademark Office*